(12) United States Patent
Djurivic

(10) Patent No.: US 7,591,856 B2
(45) Date of Patent: Sep. 22, 2009

(54) APPARATUS FOR TOTAL HIP REPLACEMENT FOR CASES OF HIP ANKYLOSIS AND SEVERE JOINT INFECTION

(76) Inventor: Zarija Djurivic, 5701 N. Sheridon Rd. #240, Chicago, IL (US) 60660

( * ) Notice: Subject to any disclaimer, the term of this patent is extended or adjusted under 35 U.S.C. 154(b) by 241 days.

(21) Appl. No.: 11/879,184

(22) Filed: Jul. 16, 2007

(65) Prior Publication Data

US 2009/0024222 A1    Jan. 22, 2009

(51) Int. Cl.
*A61F 2/32* (2006.01)
(52) U.S. Cl. .................. 623/22.11; 623/22.4; 623/23.23
(58) Field of Classification Search ............. 623/23.21, 623/23.23, 22.4, 23.26, 23.4, 22.35
See application file for complete search history.

(56) References Cited

U.S. PATENT DOCUMENTS 3,943,576 A * 3/1976 Sivash ........................ 623/23.4
6,248,132 B1 * 6/2001 Harris ...................... 623/22.15
2003/0171816 A1 * 9/2003 Scifert et al. ............. 623/22.12

* cited by examiner

*Primary Examiner*—Bruce E Snow
*Assistant Examiner*—Melissa Montano
(74) *Attorney, Agent, or Firm*—Clifford Kraft

(57) ABSTRACT

A hip replacement apparatus that normally includes a supporting rod bent into an acute angle at its center with a rounded head on one end. This supporting rod can be received at the pelvis into a pre-assembled housing with a backplate and front plate where the unit can be cemented and/or screwed into the prepared bone at the hip joint. The backplate can have an anchoring protrusion that mates into the trimmed-out bone at the joint. The front plate can have a center hole that receives, and holds the rounded head of the supporting rod from escaping. The head (and hence the supporting rod) freely rotates captively in the housing with the housing firmly attached to the pelvis. The bottom end of the supporting rod can penetrate into the center of the cut-off femur and can be cemented into the bone. The supporting rod can be held to the femur with a bone clamp apparatus including a side plate that can be banded firmly to the femur with one or a more bands.

20 Claims, 9 Drawing Sheets

APPARATUS FOR TOTAL HIP REPLACEMENT FOR CASES OF HIP ANKYLOSIS AND SEVERE JOINT INFECTION

BACKGROUND

1. Field of the Invention

The present invention relates generally to the field of hip replacements and more particularly to an apparatus for total hip replacement for cases when existing methods are not applicable such as cases with hip ankylosis or severe joint infection.

2. Description of the Prior Art

Total hip replacement or arthroplasty is a well-known surgical procedure in the medical arts. Diseased parts of the hip joint are removed and replaced with artificial parts. The most common causes of hip damage is osteoarthritis, rheumatoid arthritis and osteonecrosis (death of bone due to insufficient blood supply). The pelvis is located at the top of the legs and supports the legs. The leg bone or femur terminates in the hip joint on each side of the pelvis. The femur has a rounded head called the femoral head which fits in a socket (acetabulum) in the pelvis. This ball/socket arrangement forms a mechanical ball joint and normally allows a wide range of motion in all directions. The ball and socket of the hip joint are covered with cartilage that prevents bone to bone contact and provides a naturally lubricated joint. Hip disease many times involves damaged or missing cartilage that allows bone-to-bone contact. This can be caused by infection, injury and other causes. In severe cases, the bones of the ball and socket can fuse together to where no motion is possible.

Traditional total hip replacement involves the surgeon replacing the ball and socket joint with an artificial ball and socket. However, there are cases where traditional total hip replacement is either impossible or not recommended. These include cases of total hip ankylosis (fusion or bridging) and severe joint infections where placement of a conventional prosthesis is associated with a high risk of recurrent joint infection which can compromise the entire purpose of the replacement.

It would be advantageous to have an apparatus for total hip replacement that could be used in cases where conventional prosthesis is impossible or not recommended.

SUMMARY OF THE INVENTION

The present invention relates to a hip replacement apparatus that includes a supporting rod of stainless steel or other very strong material that is bent into an acute angle around 90 degrees at its center, and that normally has a rounded head on one end and an optional point on the other. This supporting rod can be received at the pelvis into a housing with a backplate and front plate, where the backplate is cemented and/or screwed into the prepared bone at the hip joint. The supporting rod is freely moving in the housing formed from the backplate and front plate. The backplate can have an anchoring protrusion that mates into the trimmed-out bone at the joint. The front plate can have a center hole that receives, and holds from escaping, the rounded head of the supporting rod. The head can optionally have a an elliptical shape in lateral view and a round shape in top view. The head (and hence the supporting rod) freely rotates captively in the housing with the housing firmly attached to the pelvis. The housing including the backplate, front plate and supporting rod can be pre-assembled and supplied as an integral unit for ease in installation and use.

The bottom end of the supporting rod penetrates into the center of the cut-off femur and can be cemented into the bone. The supporting rod can also be held to the femur with a bone clamp apparatus that can have a thick washer that mounts flat on the face of the cut-off femur and one or more side plates that descends downward along the side of the femur. The thick washer can have a screw hole that runs from its periphery into the center hole of the washer so that a set screw can lock the supporting rod in the washer. The supporting rod can be adjusted up and down during the procedure to adjust the leg length of the patient. The side plate can be held to the washer by the set screw through a hole that aligns with the set screw hole in the washer. The side plate can be banded firmly to the femur with one or several bands that resemble adjustable pipe bands. Two such bands are the preferred number. The bands can wrap around the femur and terminate in tightening screws on the other side of the side plate or in the side plate. Excess band can be removed during installation of the apparatus. The side plate can also optionally include several penetrating teeth that dig into the bone and grip it more firmly. In addition to the bands, optional bone screws can also penetrate the side plate into the femur.

DESCRIPTION OF THE FIGURES

Reference is now made to the following illustrations.

Several drawings and illustrations have been presented to aid in understanding the present invention. The claims are not limited to what is shown in the figures.

DESCRIPTION OF THE INVENTION

Figure 1:
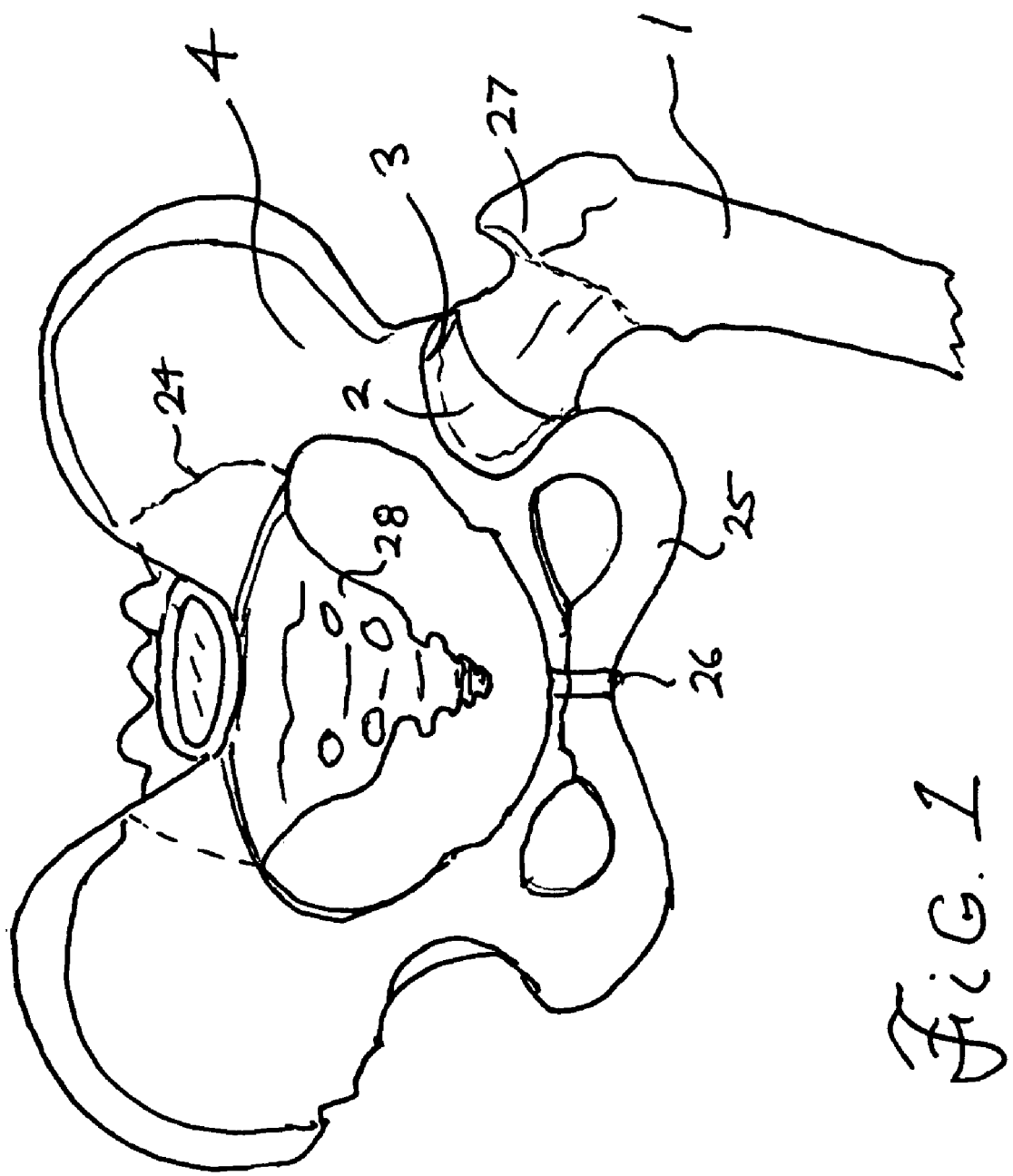
FIG. 1 shows an anterior view of a human pelvis with a hip joint.

The present invention relates to an apparatus for total hip replacement for cases of hip ankylosis and severe joint infection and other cases where standard procedures are either not possible or not advisable. Turning to FIG. 1, a schematic diagram of the human pelvis and other bones forming the human hip can be seen. The large leg bone or femur 1 connects into the pelvis 4 (illium) though a ball and socket mechanism 2,3 forming a ball joint (head of femur 2 and acetabulum 3). The ball part of the joint is the head 2 of the femur 1, while the socket 3 or acetabulum 3 is part of the pelvis. FIG. 1 also shows sacrum 28, the inferior ramus of pubis 25, the pubic symphysis 26, the sacroilliac joint 24 and the intertrochanteric crest of the femur 27.

Figure 2:
FIG. 2 shows a closer view of hip joint from FIG. 1.

This arrangement can be seen more clearly in FIG. 2 which is an enlarged drawing of the joint. The socket or acetabulum 3 is normally coated with cartilage that is naturally lubricated. This cartilage normally prevents bone to bone contact in the joint from the ball or head of the femur 2. In cases of severe joint infection or when the cartilage has been destroyed from various causes, bone to bone fusion or ankylosis can occur. This is because of the tendency of two living pieces of bone to grow together. A severe case of ankylosis can result in a joint that is totally frozen and immobile.

Figure 3:
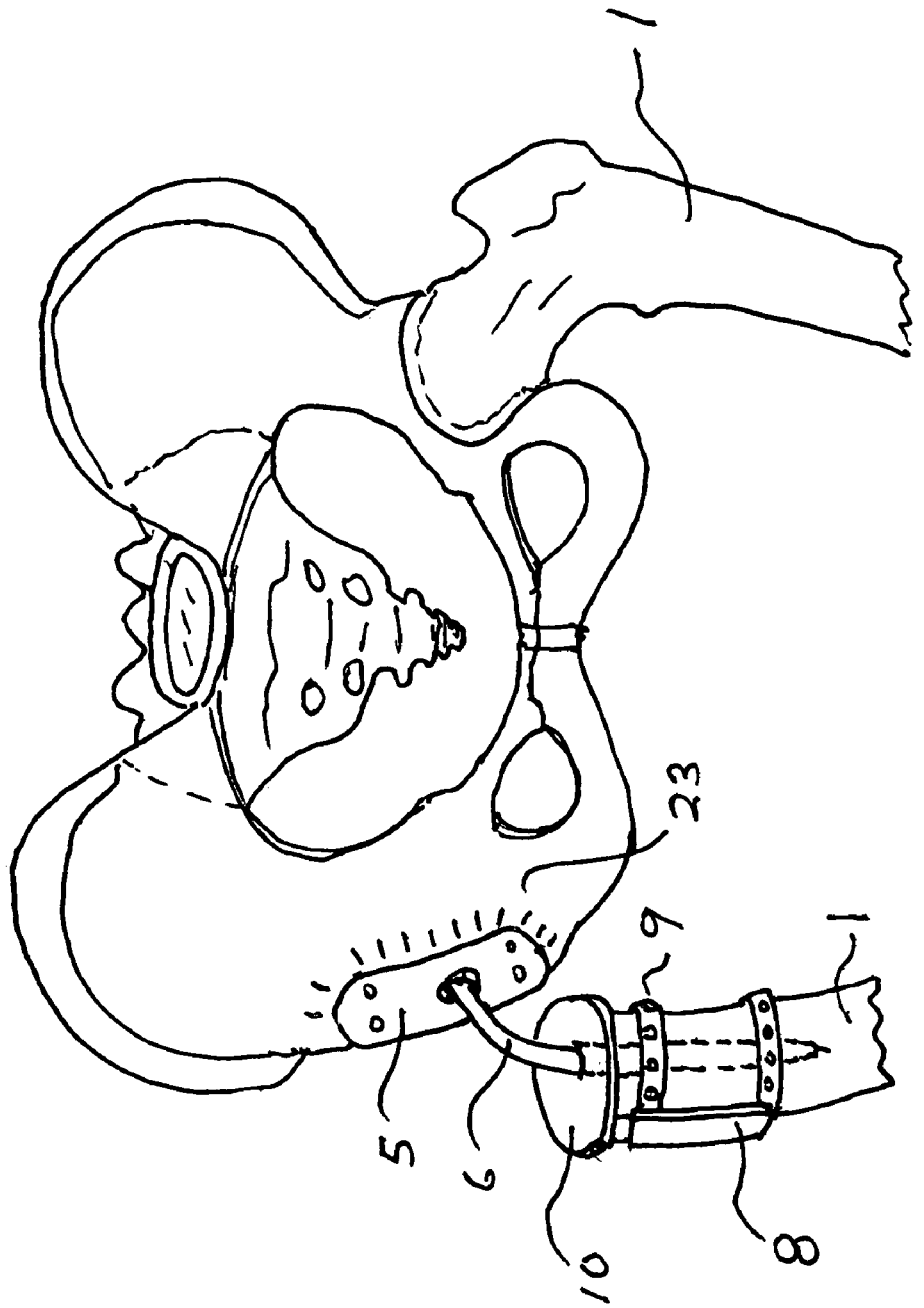
FIG. 3 shows an embodiment of the present invention installed in a human hip joint.

Normal hip replacement prosthesis devices do not work well or are impossible to implant in such cases. The present invention provides a novel apparatus for hip replacement in these cases. FIG. 3 shows an embodiment of the present invention. The femur 1 is cut using normal orthopedic methods and a special cap apparatus 8, 9, 10, or bone clamp, is installed on the end of the femur 1. A supporting rod 6 is cemented into a cavity drilled into the femur 1 and clamped to the femur 1 with at least one screw passing through a flat washer 10 that acts like a cap and by screws passing through a descending side plate 8. Bands 9, much like pipe bands known in the art, can pass around the femur 1 and be tightened with adjustment screws or other mechanisms. a receiving housing 5 receives and holds the supporting rod 6 in the joint socket. The supporting rod 6 normally includes an elliptical head the acts as a joint inside the receiving housing 5. This allows a complete range of free movement of the supporting rod 6. The housing 5 and supporting rod 6 can be supplied as an integrated unit.

Figure 4:
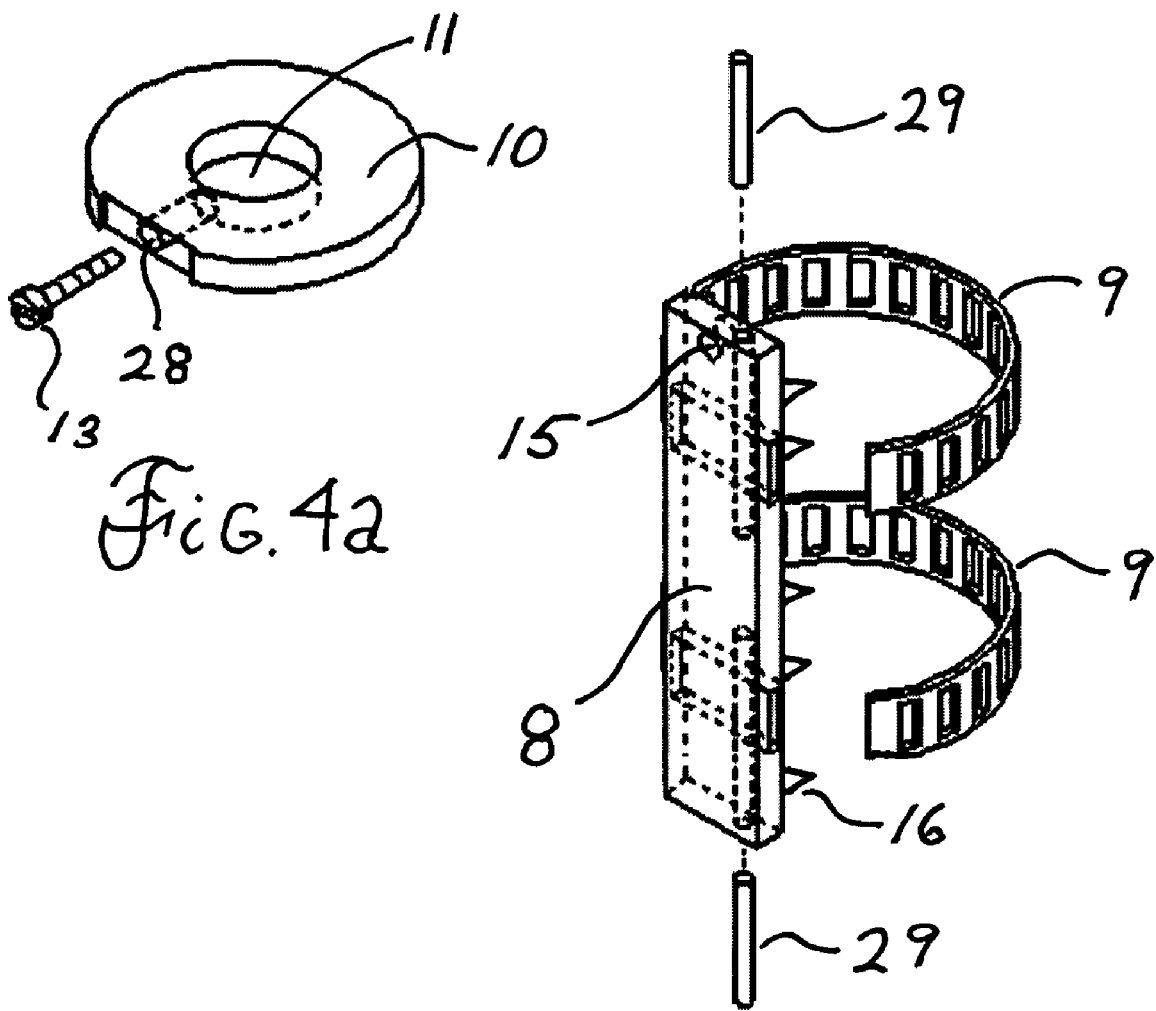
FIG. 4a shows a perspective view of a thick washer.
FIG. 4b shows a perspective view of a bone clamp.

Turning to FIG. 4a, a close-up view of an embodiment of the thick washer 10 can be seen. This thick washer 10 mounts on the top of the sawed-off end of the femur 1. It contains a central hole 11 sized to cause the supporting rod 6 to just snuggly pass through. A threaded or partially threaded through-hole 12 can be drilled and tapped through the disk part of the washer from the outermost periphery through the washer and exiting into the center hole 11. The preferred thickness of the thick washer 10 is around ⅜ inch. While this is the preferred thickness of the thick washer 10, any thickness that allows the convenient location of a set screw 13 (drilling and probably tapping) is within the scope of the present invention. The size of the set screw 13 can be chosen to match the thickness of the washer 10. Any convenient size or thread arrangement can be used. A notch or flat area 28 can be cut into the flat washer 10 to provide for mounting the side plate 8 (shown in FIG. 4b).

FIG. 4b shows a close-up view of the side plate 8. This plate contains a hole 15 at its top end to match the set screw 13 previously described. The set screw holds this plate to thick washer 10 by passing through the plate 8 and then into the washer 10 finally exiting in the center hole 11 of the washer where it clamps and holds the supporting rod 6.

The side plate 8 can optionally include multiple teeth 16 that engage the surface of the femur (engagement teeth). The side plate 8 can be attached firmly to the femur 1 with bone cement and bands 9 that pass around the circumference of the femur 1 and can be attached and tightened on the other side of the side plate 8 in a manner similar to that used for conventional hose bands. Pins or tightening screws 29 can be used to tighten and hold the bands 9 around the femur 1. While the preferred number of bands is two, other numbers of bands can be used including one or three or any number of bands needed to securely secure the side plate 8 and thick washer 10 to the femur 1.

Figure 5:
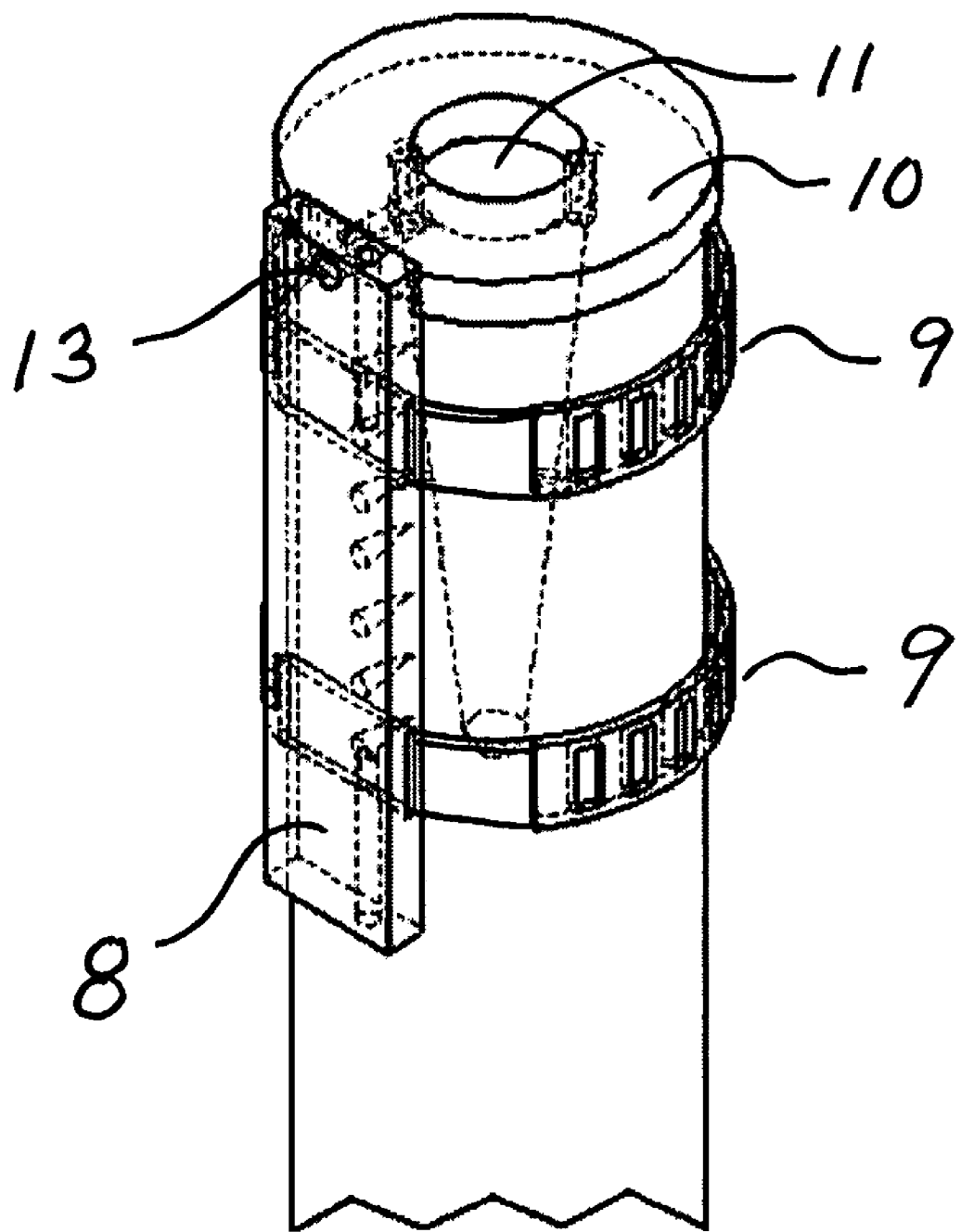
FIG. 5 shows a thick washer and bone clamp mounted on the femur.

Turning to FIG. 5, the thick washer 10 and side plate 8 can be seen mounted on the femur 1. The threaded set screw 13 passes through the side plate 8 and the thick washer 10 and into the hole 11 in the center of the thick washer 10 to clamp the supporting rod 6 that descends into the medular canal of the femur 1. The supporting rod 6 (not shown in FIG. 5) should be cemented into the medular canal with bone cement. The side plate 8 is shown in FIG. 5 banded to the femur with two bands 9 that pass around the femur 1 and terminate in tightening screws 16 in the plate 8. These tightening screws 16 work to tighten the band exactly like hose clamps. The excess band 9 can be removed after a desired tightness is achieved from both top and bottom.

Figure 6:
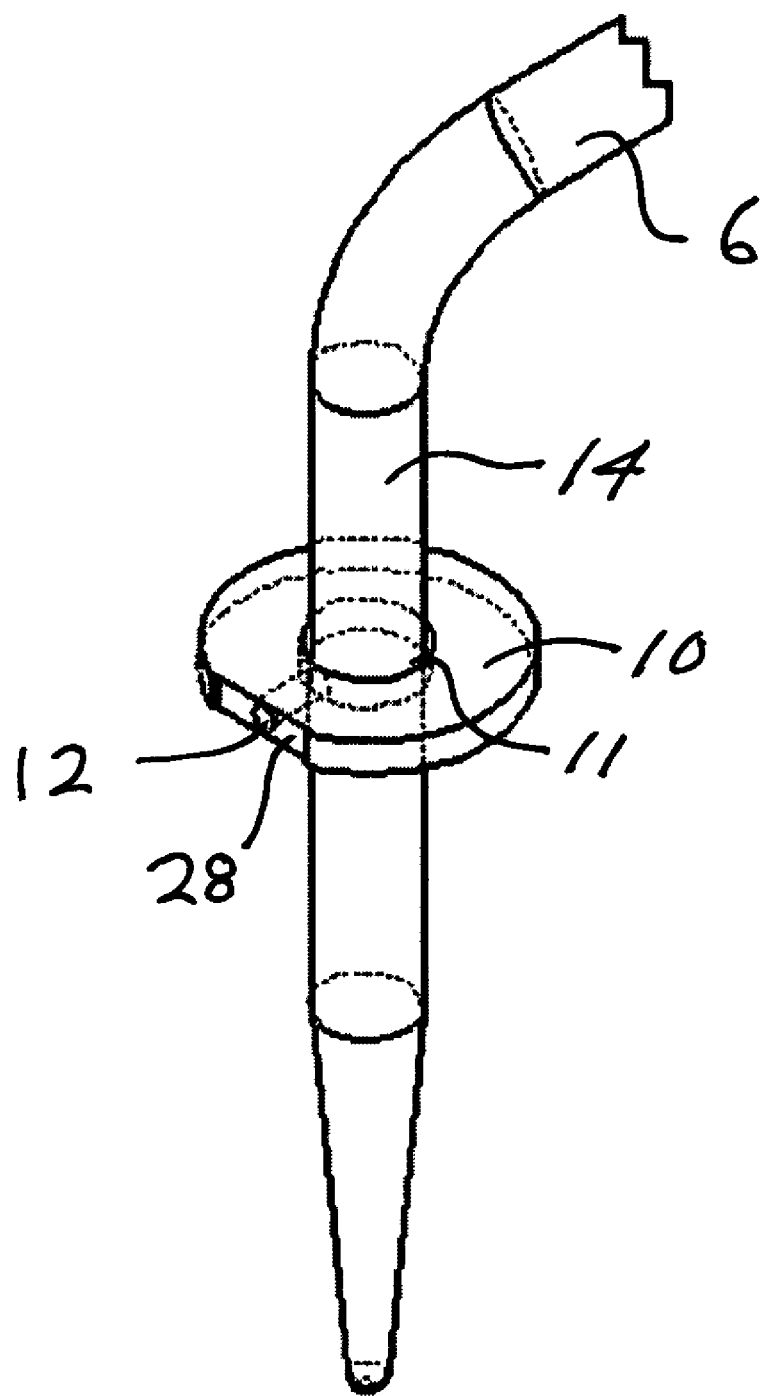
FIG. 6 shows a thick washer with supporting rod inserted.

FIG. 6 shows the lower end of the supporting rod 6 passing through the hole 11 in the thick washer 10. The hole 12 for the set screw 13 can be seen passing through the side of the thick washer 10 with the head of the screw recessed in a notch 28.

Due to the fact that a large number of patients with a condition that requires the prosthesis of the present invention also have significant shortening of the leg, it is necessary that the apparatus of the present invention be adjustable. The thick washer 10 and set screw 13 allow adjustment of the supporting rod 6 up and down before it is set into the femur 1. This requires that the outside diameter of a region 14 of the supporting rod be constant for an adjustment range. It is possible during the implantation procedure to lengthen or prolong the leg and set the supporting rod 6 in a position in the thick washer 10 that will prevent upward movement of the femur 1. In any case, the thick washer 10 prevents further shortening of the leg. The surgeon can generally adjust the length of the leg by choosing where to cut the femur and then by adjusting the supporting rod 6 in the thick washer 10 before the bone cement sets.

Figure 7A:
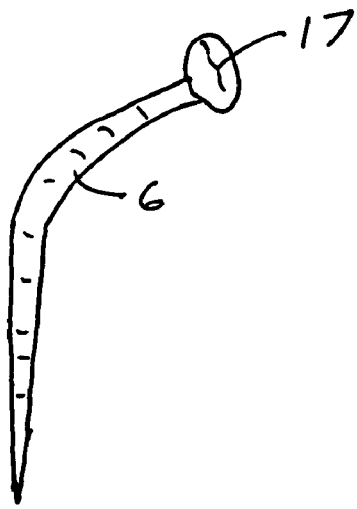
FIG. 7a shows a supporting rod from a lateral viewpoint.
Figure 7B:
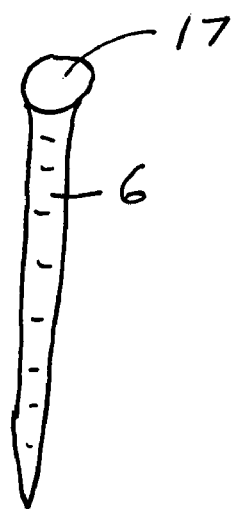
FIG. 7b shows a supporting rod from an anterior viewpoint.
Figure 7C:
FIG. 7c shows the head of a supporting rod from a lateral viewpoint.
Figure 7D:
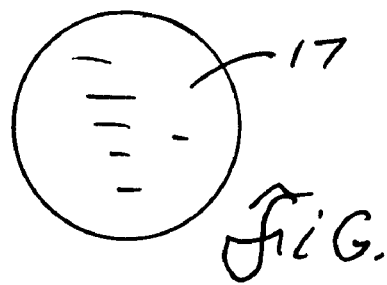
FIG. 7d shows the head of a supporting rod from a posterior viewpoint.

FIG. 7a shows a close-up side view of the supporting rod 6 with elliptical head 17. FIG. 7b shows the same view with the supporting rod 6 turned approximately 90 degrees for an end-on view. FIG. 7c shows a side view of the head 17 of the supporting rod 6, while FIG. 7d shows a top-down view of the head 17. It can be seen that top-down, the head 17 in this embodiment has a circular shape, but side-on or laterally it has a convex ellipsoidal shape. This allows it to be locked in the housing at the pelvis and yet give a complete range of movement. While this is a preferred shape, any rounded shape including a ball shape is within the scope of the present invention. In FIG. 7a, it can be seen that the supporting rod 6 is bent to an angle that allows it to be inserted into the hip joint housing. This angle can be from less than around 70 degrees to greater than around 100 degrees and can be chosen to match the needs of an individual patient. The preferred angle is around 90 degrees. Parts can be supplied with different angles.

Figure 8A:
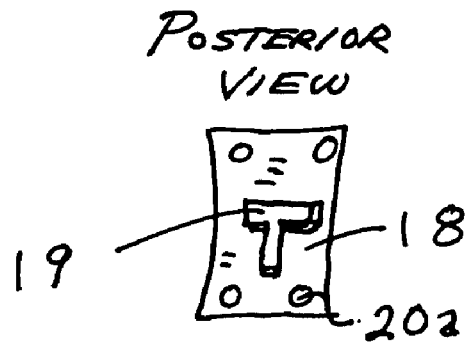
FIG. 8a shows a socket assembly from a posterior viewpoint.
Figure 8B:
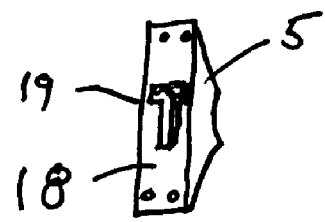
FIG. 8b shows a perspective view from slightly posterior of a socket assembly.
Figure 8C:
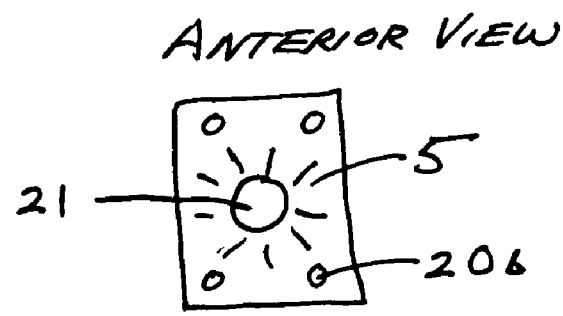
FIG. 8c shows a socket assembly from an anterior viewpoint.
Figure 8D:
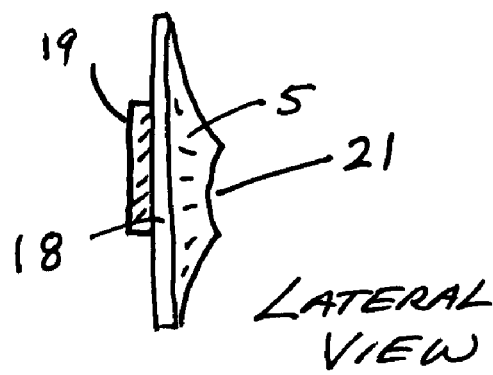
FIG. 8d shows a socket assembly from a lateral viewpoint.

Turning to FIG. 8a, a rear view of an embodiment of the backplate 18 of the support housing can be seen. This backplate mounts into the bony structure of the ankilosed joint previously separated from the neck of the femur after possibly flattening with bone cement and several bone screws that pass through holes 20a in the backplate. While the backplate 18 is shown rectangular in FIG. 8a, any shape is possible with the parts being supplied in different shapes and sizes for different patients. The bony structure remaining after the femur is cut can be trimmed in such a way that it will accept the T-shaped (or any other shape) protrusion 19 on the backplate 18. The T-shaped protrusion 19 provides an anchoring mechanism with the bone when the bone is trimmed to match it. FIG. 8b shows the housing turned to the side slightly. The T-shaped (or other shaped) protrusion 19 on the rear of the backplate 18 is optional; however, it is preferred to have some protrusion since it provides mechanical strength to the piece and prevents rotation after the backplate 18 is cemented and screwed into position. The preferred thickness of the T-shaped protruding part is around ⅜ inch; however, any convenient size may be used and is within the scope of the present invention. FIGS. 8b-8c also show the front plate of the housing 5 mounted to the backplate 18. FIG. 8c is a front view showing the receiving hole 21 for the supporting rod 6. The front plate 5 can be supplied with screw holes 20b arranged to mate with the holes 20a in the backplate 18. The unit can be assembled by first placing the supporting rod 6 through the receiving hole 21 in the front plate 5, and then cementing and screwing the unit into the prepared joint bone. While this is a method of using the apparatus, it is the preferred method that the backplate 18 and front plate 5 be supplied as a pre-assembled unit with the supporting rod 6 pre-installed. This makes the present invention easier to use and to mount. The front and back plates can be welded or coupled by any coupling means known in the art.

Figure 9:
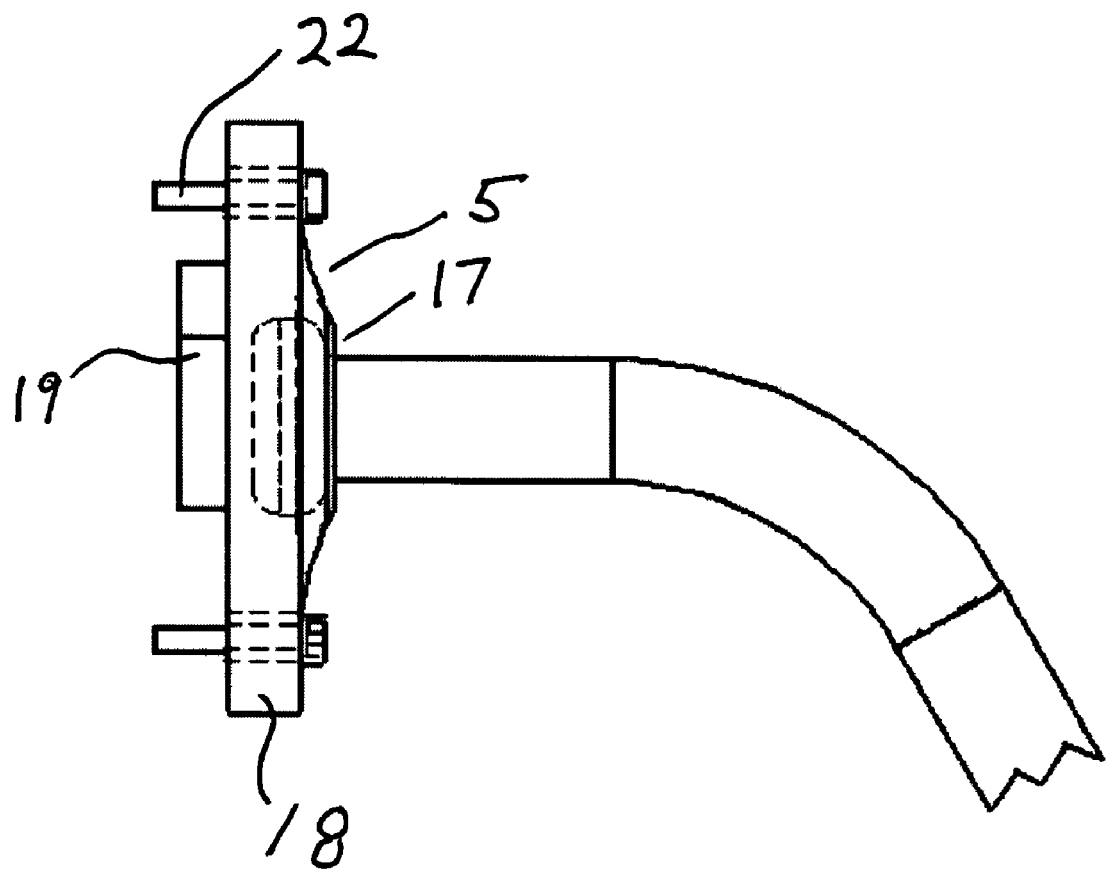
FIG. 9 shows a section of a socket assembly with a supporting rod in the socket.

FIG. 9 shows a sectional view the assembled unit with the supporting rod 6 passing through the receiving hole 21 of the front plate 5 with the head 17 of the supporting rod inside the housing unit free to move. The unit is shown attached to the bone with bone screws 22. The preferred material for the housing and supporting rod is stainless steel; however, any strong material may be used including, but not limited to, strong polymers, carbon composites, titanium, various allows of metals and any other material that will not break under the expected stresses and will not allow the head 17 of the supporting rod 6 to tear or shear out of the front of the housing 5. The preferred cement is bone cement know and used in the medical arts; however, any suitably strong epoxy or polymer cement may be used and is within the scope of the present invention. Any type of strong screws may be used with stainless steel bone screws being preferred. No material should be used that will corrode or interact unfavorably with the human body or normal body fluids.

The total hip replacement apparatus of the present invention provides a prosthesis that can be used when existing methods are either not applicable or recommended, for example in the case of total hip ankylosis or severe joint infection. The present invention provides a hip replacement that requires minimal muscle dissection and trauma along with minimal preparation of the bone for placement of the back plate. In this part of the procedure, the surgeon will have no major problems with bleeding. The housing, backplate and supporting rod can be supplied as a single pre-assembled, integral unit for ease of use.

Several descriptions and illustrations have been provided to aid a skilled person to understand the present invention. A person with skill in the art will realize that there are numerous changes and variations that can be made without departing from the spirit of the invention. Each of these changes and variations is within the scope of the present invention.

I claim:

1. A total hip replacement apparatus comprising:
    an elongated supporting rod with an upper part and a lower part, said supporting rod bent to an angle with respect to said upper and lower parts, the upper part of said supporting rod terminating in a head;
    a support housing engaging the head of said elongated supporting rod, said support housing having a front and back surface, the supporting rod passing through said front surface;
    a bone clamp for receiving the lower part of said supporting rod, said bone clamp adapted to clamp a human femur;
    said bone clamp, said supporting rod and said support housing providing a freely rotatable hip replacement joint.

2. The hip replacement apparatus of claim 1 wherein said supporting rod is bent to an angle near 90 degrees.

3. The hip replacement apparatus of claim 1 wherein said head is elliptical in lateral view and circular in top-down view.

4. The hip replacement apparatus of claim 1 wherein said support housing has an anchoring protrusion on its back surface.

5. The hip replacement apparatus of claim 4 wherein said anchoring protrusion is T-shaped.

6. The hip replacement apparatus of claim 1 wherein said bone clamp includes a washer, said washer being mounted on a cut femur face.

7. The hip replacement apparatus of claim 1 wherein said bone clamp comprises a washer and a side plate, said washer being mounted on a cut femur face and said side plate being mounted on the cortex of said femur.

8. The hip replacement apparatus of claim 7 wherein said side plate contains a plurality of engagement teeth.

9. The hip replacement apparatus of claim 7 wherein said washer receives said supporting rod through a center hole.

10. The hip replacement apparatus of claim 9 wherein said washer further contains a screw hole running from its periphery to its center wherein a set screw can be inserted in said hole clamping said supporting rod.

11. The hip replacement apparatus of claim 7 wherein said side plate clamps said femur with at least one adjustable band.

12. The hip replacement apparatus of claim 1 wherein the lower part of said supporting rod is pointed.

13. A hip replacement apparatus of the type used in cases of total bone bridging or severe joint infection where conventional prosthesis generally cannot be used, the apparatus comprising an elongated rod with an upper and lower end bent to an angle where the upper end contains a rounded head and this head is received in a housing with a front plate and a back plate, and where this housing can be cemented and/or screwed to a hip joint bone, the housing having a hole in its front plate to receive the rod in a manner that allows the rod to rotate but not escape the housing, the lower end of the rod being cemented into the medular canal of a cut femur with the lower end of the rod also being held in the femur by a rod clamp apparatus that securely clamps the rod to the femur.

14. The hip replacement apparatus of claim 13 wherein the rod clamp apparatus comprises a washer attached to a plate where the washer mounts on a flat top face of the cut femur and the plate descends along the rod and is attached by at least one band around the femur and where the rod passes through the washer and the washer contains a set screw that clamps the rod securely.

15. The hip replacement apparatus of claim 14 wherein the plate contains a plurality of engagement teeth to engage the femur.

16. The hip replacement apparatus of claim 13 wherein the back plate of the housing includes an anchoring protrusion.

17. A hip replacement apparatus comprising:
    an elongated supporting rod bent to an acute angle with a head elliptical in lateral view and round in top view and a pointed lower end;
    a support housing receiving the head of said supporting rod, wherein the head is free to rotate in said support housing;
    said support housing having a front surface with a hole for receiving said supporting rod and a back surface, said front and back surfaces screwed and/or cemented to pelvis hip joint bone, said back surface further having an anchoring protrusion on its posterior face;

a bone clamp adopted to attach to a cut-off human femur that receives the lower end of said supporting rod through a hole in a washer where the washer is mounted on a face of said cut-off femur, and said supporting rod is cemented into a cavity in said femur, said supporting rod being clamped in said washer, said bone clamp further comprising a side plate mounted on a side of said femur with at least one band passing around said femur.

18. The hip replacement apparatus of claim 17 wherein said acute angle is around 90 degrees.

19. The hip replacement apparatus of claim 17 wherein said supporting rod is clamped in said washer with a set screw.

20. The hip replacement apparatus of claim 17 wherein said anchoring protrusion is T-shaped.

* * * * *